(12) United States Patent
Wright et al.

(10) Patent No.: US 6,928,316 B2
(45) Date of Patent: Aug. 9, 2005

(54) METHOD AND SYSTEM FOR HANDLING COMPLEX INTER-DEPENDENCIES BETWEEN IMAGING MODE PARAMETERS IN A MEDICAL IMAGING SYSTEM

(75) Inventors: Kenneth M. Wright, San Jose, CA (US); Anja Shvarts, San Jose, CA (US); Stefan J. A. Schmitz, Milpitas, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 219 days.

(21) Appl. No.: 10/610,291

(22) Filed: Jun. 30, 2003

(65) Prior Publication Data

US 2004/0267117 A1 Dec. 30, 2004

(51) Int. Cl.⁷ .............................. A61B 5/05; A61B 8/00; G06F 17/00
(52) U.S. Cl. ..................... 600/407; 600/437; 707/103 Y
(58) Field of Search ................................. 600/407, 410, 600/425, 437, 443, 447; 707/102, 103 R, 103 Z (56) References Cited

U.S. PATENT DOCUMENTS

| | | | |
|---|---|---|---|
| 5,379,642 A * | 1/1995 | Reckwerdt et al. ............ 73/625 |
| 5,482,046 A * | 1/1996 | Deitrich ....................... 600/458 |
| 5,549,111 A * | 8/1996 | Wright et al. ................ 600/443 |
| 5,797,846 A * | 8/1998 | Seyed-Bolorforosh et al. ........................... 600/447 |
| 5,919,136 A * | 7/1999 | Rao et al. ..................... 600/431 |
| 6,174,287 B1 * | 1/2001 | Resnick et al. .............. 600/458 |
| 6,511,426 B1 * | 1/2003 | Hossack et al. ............. 600/437 |
| 6,679,844 B2 * | 1/2004 | Loftman et al. ............ 600/443 |
| 6,733,554 B2 * | 5/2004 | Ribera Salcedo et al. ..... 55/338 |
| 2003/0097065 A1 * | 5/2003 | Lee et al. ................... 600/437 |
| 2003/0208118 A1 * | 11/2003 | Abe et al. ................... 600/407 |
| 2004/0044279 A1 * | 3/2004 | Lewin et al. ................ 600/407 |

OTHER PUBLICATIONS

Applications Programming in Smalltalk–80 (TM); How to use Model–View–Controller (MVC)☐☐(http://st–www.c-s.uiuc.edu/users/smarch/st–docs/mvc.html) (Document Copy in case file).*
Model–View–Controller☐☐(http://ootips.org/mvc–pattern.html) (Document Copy in case file).*
Applications Programming in Smalltalk–80 (TM): How to use Model–View–Controller (MVC)—printed from the Internet at: http://st–www.cs.uiuc.edu/users/smarch/st–docs/mvc.html 1987, 1992, Steve Burbeck, Ph.D., 11 pages.
Model–View–Controller—printed from the Internet at: http://ootips.org/mvc–pattern.html, May 14, 1998, 3 pages.

* cited by examiner

*Primary Examiner*—Francis J. Jaworski (57) ABSTRACT

The preferred embodiments described herein provide a method and system for handling complex inter-dependencies between imaging mode parameters in a medical imaging system. In one preferred embodiment, a behavior engine comprises a plurality of behavior objects interconnected by parameters with at least one of the parameters being circularly dependent. A static list of the behavior objects and the dependent parameters is generated. After an input to the medical imaging system causes one parameter to change values, a dynamic list of behavior objects dependent on the changed parameter is generated. Further, an iterative process of processing the behavior objects in the dynamic list, determining whether any output parameters from the processed behavior objects have changed, adding behavior objects to the dynamic list which are dependent on the changed parameter outputs, and removing the processed behavior objects from the dynamic list is performed. The iterative process may be performed until the dynamic list does not contain any behavior objects.

21 Claims, 4 Drawing Sheets

METHOD AND SYSTEM FOR HANDLING COMPLEX INTER-DEPENDENCIES BETWEEN IMAGING MODE PARAMETERS IN A MEDICAL IMAGING SYSTEM

BACKGROUND

The model-view-controller paradigm is a design pattern often used by applications as a flexible model for object oriented graphics applications. One such application is for graphical applications in an ultrasound system. The paradigm separates the system into three primary elements: (1) model; (2) view; and (3) controller.

The model is an abstract representation of the state of the system. It encapsulates data and functions that operate on it, and serves as a computational approximation or abstraction of a real world process or system. In effect, the model captures the state of a process or system, and how the system works. Typically, there is only one model per system. The model, as an object, has no specific methods associated with it for the interpretation of the information it contains but exists as a high-speed repository of information. One example of a model is a parameter cache, which is a global repository for all of the imaging mode parameters (parameters) in the system. The parameters may be interpreted as representing the state of the system, such as an ultrasound system. In actuality, the parameters are used not only to represent the state of the ultrasound system, but also to represent the state of the application itself. In this manner, the parameters may be viewed as a global database.

The view is a graphic representation of the model, suitable for a user interface or display. The view manages the graphical and/or textual output to the portion of the bit-mapped display that is allocated to its application. A view may have a one to one correspondence with a display, knowing how to render to the display. A view attaches to a model and renders its contents to the display. In addition, when the model changes, the view may automatically redraw the affected part of the image to reflect those changes. In an ultrasound system, the view may be represented by visibles and the objects that map them on and off the screen.

The controller is the means by which the user interacts with the application. The controller accepts input from the user and commands the model and/or view to change based on that input. In essence, the controller is responsible for mapping end-user action to application response. For example, if the user modifies an input to the system, such as an input from the keyboard, etc., the controller determines how the application should respond. The controller, thus, directs how to bind the elements of a view to a model, and how to interpret events in the system to change both the model and the view. The controller is typically where the majority of the software code resides in a system based on the model-view-controller paradigm. In the case of an ultrasound system, the controller may be composed of four primary engines: the behavior engine, the user function handler, the data field manager, and the graphics engine.

The behavior engine is responsible for executing the behavior of the User Interface/System Control software subsystem in an ultrasound system. It may comprise a list of behavior objects (BOs). Each behavior object may have a set of zero or more input and output parameters.

Figure 1:
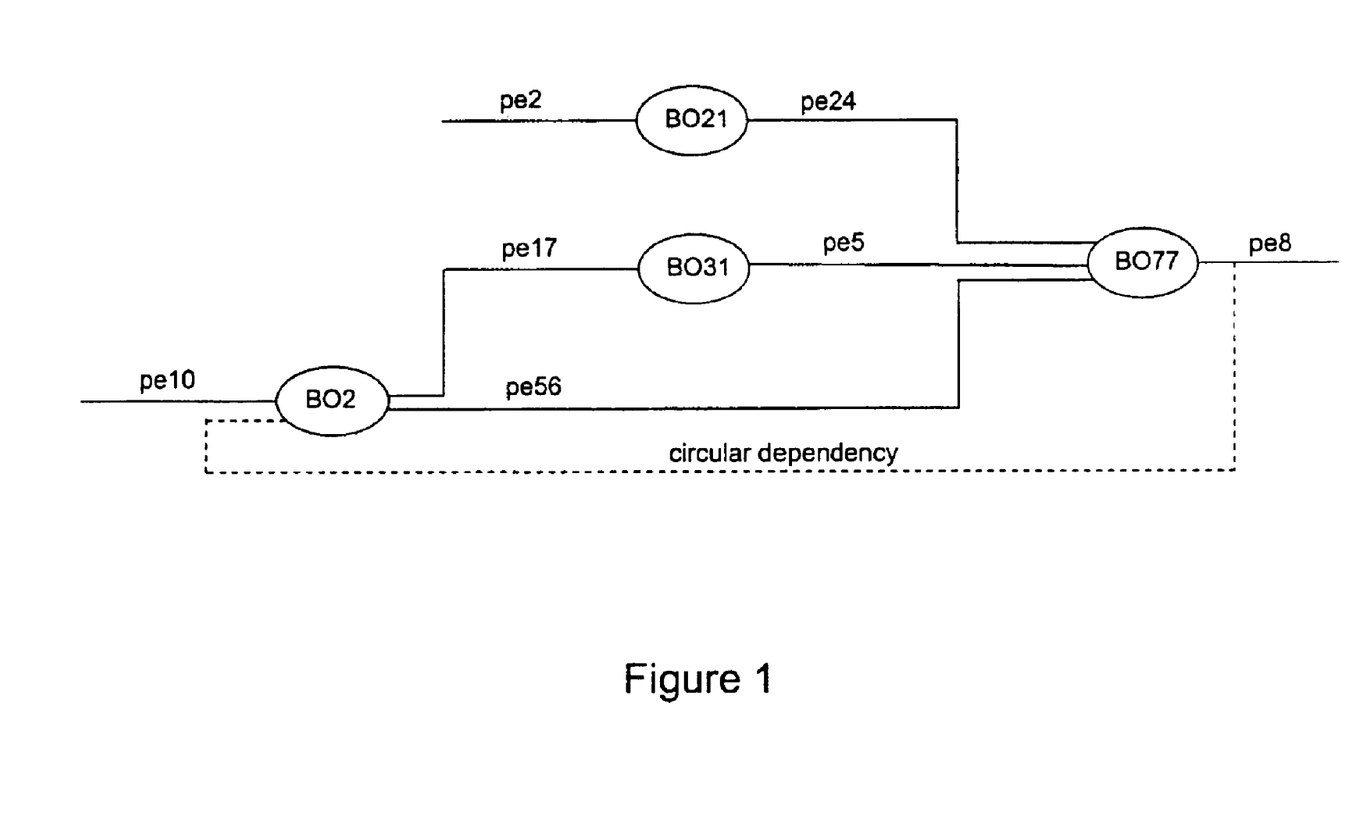
FIG. 1 is a block diagram of behavior objects in a behavior engine with circular dependency.
Figure 2:
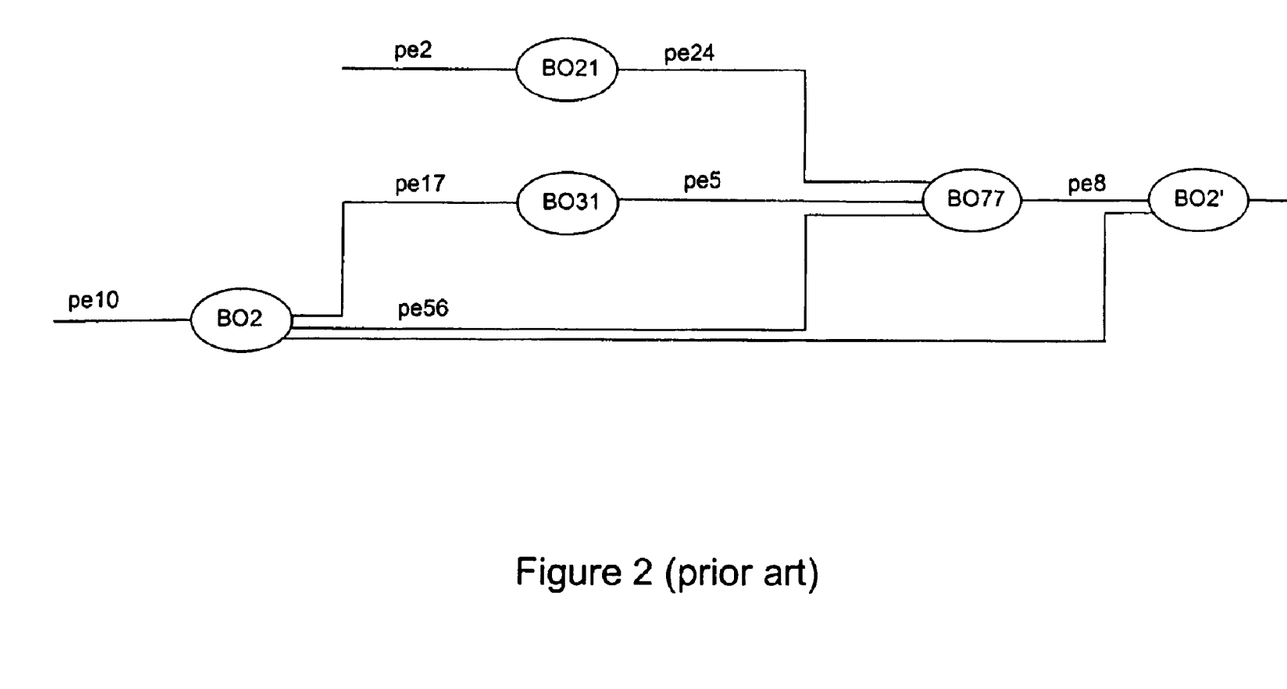
FIG. 2 is a block diagram of behavior objects in a behavior engine after using a leveling process.

Software subsystem control, such as in the ultrasound machine, is very complex and its features are inter-dependent. The complexities may require that some of the behavior engines in the system include circular dependencies. Referring to FIG. 1, there is shown a block diagram of an example of a circular dependency. The example is offered merely for a simple illustration. As shown in the figure, pe8 is an output parameter to BO77 and is an input to BO2. Due to the complexities, prior behavior engines did not include circular dependencies in the behavior objects. Instead, when a behavior engine required a circular dependency, a "leveling process" was used to remove the circular dependency. The leveling process would introduce one or more new behavior object(s) which would account for the circular dependency, thereby simplifying the system. Referring to FIG. 2, there is shown a prior art block diagram in which a leveling process is used. To account for the circular dependency, an additional behavior object, BO2' is created which may be based on the behavior logic from BO2. However, there are drawbacks to using the leveling process. First, one is required to replace the circular dependency with one or more new behavior object(s) and one or more additional parameters. Second, as more circular dependencies are required, the leveling process becomes exceedingly complicated. Third, the leveling process requires that the sequence of updating the behavior objects is fixed, with a one pass execution for all behavior objects. The sequence is predetermined when initializing the system so that, when there is a change to a parameter in the system, all behavior objects (including the analysis of all input parameters for algorithm updates for the given behavior object), and not just affected behavior objects, are updated. In effect, the updating must begin at the left side of FIG. 2 and end at the right side of FIG. 2. This type of updating is overly rigid and very inefficient.

There is a need, therefore, for an improved method and system for handling circular dependencies in a behavior engine.

SUMMARY

The present invention is defined by the following claims, and nothing in this section should be taken as a limitation on those claims.

A behavior engine in a medical imaging system may comprise a plurality of behavior objects interconnected by parameters, with at least one of the parameters being circularly dependent. Input to a medical imaging system, such as user or system input, may change one or some of the parameters in the behavior engine. In one aspect, the changes to the parameters in the behavior engine are determined dynamically in order to account for any circularly dependent parameters. One example of this is by creating a dynamic list of behavior objects affected by the changed parameter, and through iterative processing, determining other affected parameters and behavior objects in the behavior engine.

The dynamic list may initially include the behavior objects dependent on the changed parameter. Further, the iterative process may process the behavior objects in the dynamic list; determine whether any output parameters from the processed behavior objects have changed; add behavior objects to the dynamic list which are dependent on the changed parameter outputs; and remove the processed behavior objects from the dynamic list. This iterative process may continue until the dynamic list does not contain any behavior objects. In this manner, fewer than all of the behavior engines need to processed in order to determine changes to the parameters in the behavior engine. Moreover, the changes to the parameters in the behavior engine may be determined even if the behavior engine includes circularly dependent parameters.

DETAILED DESCRIPTION OF THE PRESENTLY PREFERRED EMBODIMENTS

Figure 3:
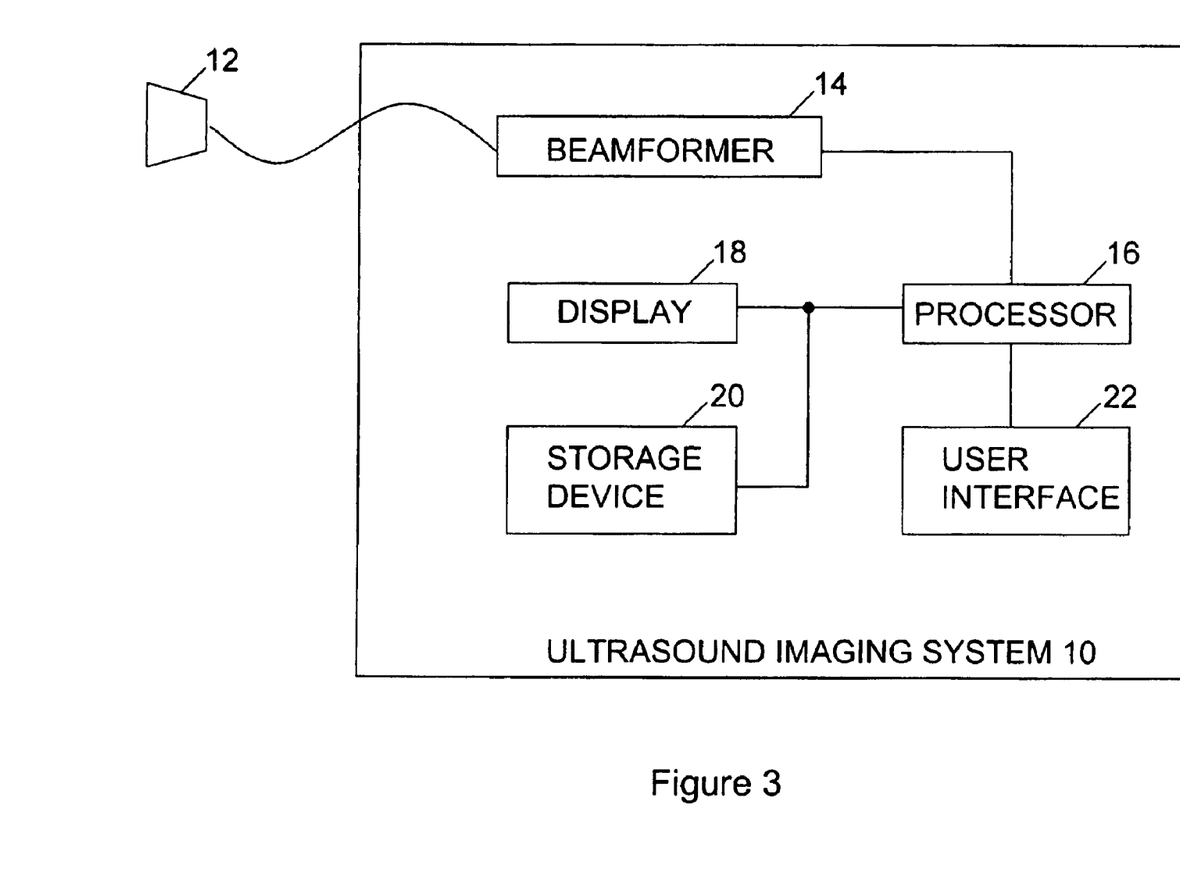
FIG. 3 is a block diagram of a medical diagnostic ultrasound imaging system of a preferred embodiment.
Figure 4:
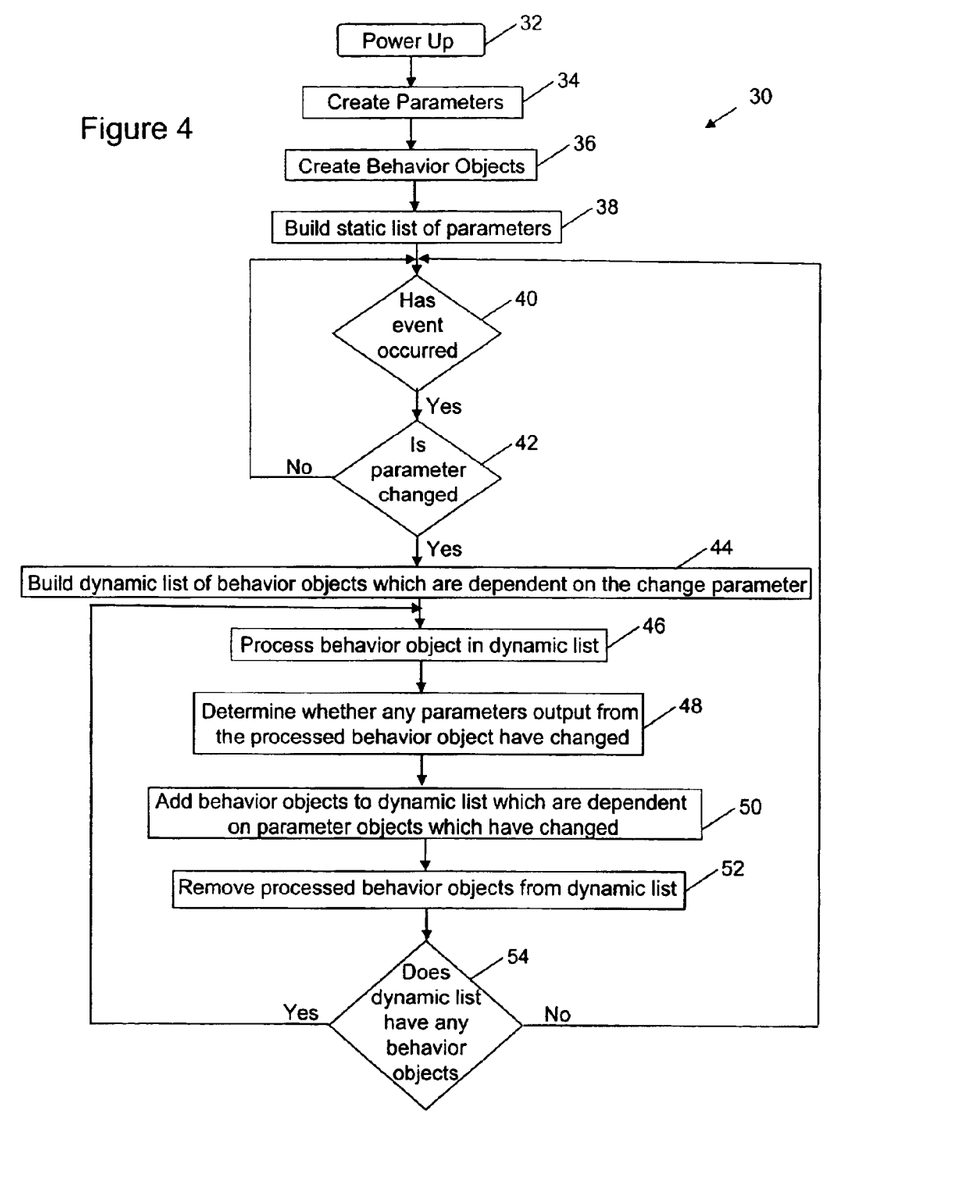
FIG. 4 is a flow chart of a method of a preferred embodiment for event processing.

Turning to the drawings, FIG. 3 is a block diagram of a medical diagnostic ultrasound imaging system 10 that is used to illustrate the operation of the method shown in FIG. 4. While an ultrasound system and ultrasound images are used in this illustration, it should be noted that other types of medical image acquisition devices and medical images can be used with these preferred embodiments. As shown in FIG. 3, the ultrasound system 10 comprises a transducer probe 12, a beamformer 14, a processor 16, a display device 18, a storage device 20, and a user interface 22. The term "processor" broadly refers to the appropriate hardware and/or software components of the ultrasound system 10 that can be used to implement the functionality described herein. The storage device 20 is suitable for storing digital images and may take the form, for example, of a solid-state volatile or non-volatile memory device or a permanent or removable optical or magnetic disk. The user interface 22 can include, for example, physical knobs, buttons, or keys that a user can physically manipulate on a control panel; soft buttons displayed on the display device 18 that a user can select with a pointing device or by touching the displayed button if the display device 18 is touch-sensitive; or a microphone through which a user can voice commands. As discussed in more detail below, user action, such as user input via the user interface 22, which leads to event processing, may result in the writing to some parameters in the behavior engine. Alternatively, system action, such as the plugging of transducer probe 12, which leads to event processing, may also result in the writing to some parameters in the behavior engine.

The ultrasound system 10 may comprise additional components, which are not shown in FIG. 1 for simplicity. For example, the ultrasound system 10 may comprise an additional memory device (computer-usable media) that stores software (computer-readable program code) run by the processor 16.

In operation, a sonographer uses the user interface 22 to select a set of acquisition time controls settings. As used herein, the term "set" refers to a group of one or more, and the term "acquisition time control" refers to any control that a user manipulates in the process of acquiring a medical image to affect how the medical image is acquired. Manipulating an acquisition time control can affect transmit, receive, and/or processing operations. For a medical diagnostic ultrasound imaging system, an acquisition time control can be a "major mode" key that a user selects to choose the type of ultrasound image that will be generated (e.g., M-mode, B-mode, color flow, or Spectral Doppler (PW)). An acquisition time control can also be a flow sub-mode with Doppler Tissue Imaging or contrast imaging settings. Additionally, an acquisition time control can be an individual parameter (e.g., frequency or depth) or a "pre-set," which is a stored combination of individual acquisition time control settings (e.g., specific mode, frequency, and depth settings) grouped together based on the anatomy being imaged (e.g., general radiology, vascular examination, cardiology) or the sonographer performing the examination (e.g., Dr. Smith, Dr. Robert).

During an ultrasound examination, the sonographer contacts the transducer probe 12 with a patient, and the ultrasound system 10 acquires an ultrasound image in accordance with the acquisition time control settings. In general, the ultrasound system's processor 16 causes the beamformer 14 to apply a voltage to the transducer 12 to cause it to vibrate and emit an ultrasonic beam into the portion of the patient's body in contact with the transducer 12. Ultrasonic energy reflected from the patient's body impinges on the transducer 12, and the resulting voltages created by the transducer 12 are received by the beamformer 14. The processor 16 processes the sensed voltages to create an ultrasound image and displays the image on the display device 18. As discussed in more detail below, the processor 16 may process an event, such as a user input or a system input, by accessing the model-view-controller, including the behavior engine, to display the image on the display device 18. For example, upon an input to the system, the processor 16 may call an event handler, which may change a parameter or several parameters based on the input to the system. The changing of a parameter begins a transaction for processing the input to the system.

In addition to being displayed on the display device 18, a generated ultrasound image can also be stored in digital form. For example, the sonographer can be given the option of storing an ultrasound image by pressing an "image capture" key on the user interface 22, or, alternatively, the ultrasound image can be automatically stored without user intervention. In this way, a series of images from an ultrasound exam can be stored in the storage device 20 in the ultrasound system 10 for later review. While shown as a single box in FIG. 1, the storage device 20 can comprise one or more individual storage devices (e.g., two separate disks). Additionally, an ultrasound image can be stored in a storage device external to the ultrasound system 10.

Referring to FIG. 4, there is shown a flow chart 30 of a method of a preferred embodiment for event processing. The ultrasound system 10 is powered up, as shown block 32. After power up, the list of parameters is accessed, as shown at block 34, so that the parameters may be instantiated. Further, the behavior objects are accessed, as shown at block 36, so that the behavior objects may be instantiated. A behavior object may comprise an algorithm or a series of algorithms which have parameters as inputs and as outputs. Based on the parameters and the behavior objects, a static list of parameters may be created during initialization, as shown at block 38. The static list may include, for each parameter in the system, a Parameter Output Agent (outputs from a behavior object) and zero or more Parameter Input Agent(s) (inputs to a behavior object). During the initialization, if a parameter is a Parameter Output Agent, it is added to the parameter list as the parameter owner. Moreover, if a parameter is a Parameter Input Agent, it is added to the parameter list as a dependent Parameter Input Agent. These terms are discussed in more detail below. An example of a static list, for the behavior engine shown in FIG. 1, is provided in Table 1.

TABLE 1

| pe8 | pe2 | pe17 | pe56 | pe24 | pe5 | pe10 |
|---|---|---|---|---|---|---|
| Parameter Output Agent for BO77 | <not shown> | Parameter Output Agent for BO2 | Parameter Output Agent for BO2 | Parameter Output Agent for BO21 | Parameter Output Agent for BO31 | <not shown> |
| Parameter Input Agent for BO2 | Parameter Input Agent for BO21 | Parameter Input Agent for BO31 | Parameter Input Agent for BO77 | Parameter Input Agent for BO77 | Parameter Input Agent for BO77 | Parameter Input Agent for BO2 |

The terms (pe) are the parameters, with pe8 representing parameter 8, for example. Table 1 further includes whether the parameter is an output from or an input to a behavior object. For example, Parameter Output Agent for BO77 represents that pe8 is an output from Behavior Object 77. Further, Parameter Output Agent for BO77 is the parameter owner. As another example, Parameter Input Agent for BO2 represents that pe8 is an input to Behavior Object 2, and represents a dependent Parameter Input Agent. Thus, Table 1 shows a static list of all parameters in the system, listing the "dependent" behavior objects (i.e., dependent either as an input to or an output from a behavior object). Moreover, Table 1 includes one Parameter Output Agent and one Parameter Input Agent for each parameter. Typically, there is one Parameter Output Agent (parameter owner) and there can be multiple Parameter Input Agents (although only one is shown for each parameter in Table 1). As shown in Table 1, the static list correlates the behavior objects with the input and output parameters. Other configurations for a static list may correlate the behavior objects with the input and output parameters.

The static list may be generated after each power-up for the ultrasound system and stored in volatile memory in storage device 20. Alternatively, the static list may be generated and stored in non-volatile memory in storage device 20 so that the static list need not be created after each power-up.

After the static list is accessible (either in volatile or non-volatile memory), the system is reviewed to determine whether an event has occurred, as shown at block 40. As discussed above, an event may occur based on a user or system input. For example, the user may enter input via the user interface 22. The input to the system causes processor 16 to call event handler. If necessary, the event handler changes a parameter or several parameters based on the input. If the event handler has changed a parameter, processing of the change occurs, as shown at block 42. If no parameter has been changed, the flow diagram loops back to block 40.

The processing of an event, by the Behavior Engine or the engine that drives updates during a transaction, analyzes which parameters have been changed, or become dirty, during the transaction. Typically, the parameters which may change due to user input are not those that are a parameter output agent (an output to a behavior object). For example, in FIG. 1, the parameter which may change due to user input may include pe2 or pe10. Alternatively, other parameters, which are parameter output agents (outputs to behavior objects), may change and initiate a transaction as well. In this model, the parameters representing the state of the system are updated in order based on their owner's registered input dependencies. Behavior objects with dependent parameters may be updated after the behavior object that has registered output interest input that parameter. The order of the behavior objects' updates are stored in a simple linear array, based on the static list created at initialization, and are updated during a transaction by a Behavior Engine whenever any of the registered input parameters have been changed during the transaction. In this manner, the changed parameters may determine which behavior objects are updated, rather than processing all behavior objects in a fixed, predetermined manner. The following example focuses on a change based on a user input, so that the changed parameter which initiates the transaction is not a parameter output agent. Subsequently, parameter output agents which change and initiate a transaction are discussed.

Based on the parameters that have changed, a dynamic list is built of the behavior objects which are dependent on the changed parameters, as shown at block 34. Thus, the processing of a transaction does not solely rely on a static list of dependent behavior objects based on parameter dependencies. Rather, as discussed in more detail below, the processing of circular dependencies creates and uses a dynamic list of changed parameters for a given transaction, and passes that list to an interested behavior object during the update cycle. Changed parameters may be added to an interested behavior objects' "dynamic list" as they are output by another behavior object (assuming that the parameter has, in fact, changed value). When a behavior object is passed this list of changed parameters, it may or may not receive all of the parameters that it is interested in at one time for that transaction, so that the engine that drives the transaction can continue to send changed parameter lists again until there are no more changed parameters. Further, because a behavior object can be updated more than once per transaction, it can handle circular dependencies. This assumes that there are no positive feedback loops designed into the dependency network, which would be a design flaw. This further assumes that a given behavior object cannot register both input and output interest in a single parameter.

In the example shown above in Table 1, assume an event processing has changed parameter 2 (pe2). As shown in Table 1, pe2 has as its parameter input agent BO21. When pe2 is changed, the dynamic list of dependent behavior objects for the current transaction initially is as follows:

| Parameter Input Agent for BO21 | → behavior objects in dynamic list |
|---|---|
| pe2 | → dynamic list of parameters |

After the dynamic list is created, the behavior engine initiates the transaction and enters an iterative loop. The transaction controller, which processes the entire transaction from the initial user input to final rendering of the image, processes the behavior object(s) in the dynamic list, as shown at block 36. The processing of the behavior object may invoke the algorithms associated with the particular behavior object. In one aspect, only the algorithms which are dependent on a changed input parameter are processed. For example, the particular behavior object may include over one hundred algorithms. The particular behavior object may further include one, some, or several input parameters (Parameter Input Agents). If only one of the input parameters is changed, only the algorithms in the particular behavior object that are dependent on the changed input parameter are processed. This allows for more efficient processing since a subset of the algorithms (which are dependent on changed input parameters) are processed, rather than all the algorithms in the behavior object.

Based on the processing of the behavior object(s), other parameters which are output from the processed behavior object(s) may be affected. Thus, it is determined which parameters output from the processed behavior objects have changed, as shown at block 38. Then, the behavior objects which depend on the changed parameters are added to the dynamic list, as shown at block 40.

In the example shown above, behavior object 21 (BO21) is updated because it depends on pe2. Assuming that the updating of BO21 causes a change in pe24 (an output to BO21, as shown in FIG. 1), the change in pe24 means that BO77, which has pe24 as an input, is added to the dynamic list, as follows:

| Parameter Input Agent for BO21 | Parameter Input Agent for B077 | → behavior objects in dynamic list |
|---|---|---|
| pe2 | pe24 | → dynamic list of parameters |

The processed behavior objects are removed from the dynamic list, as shown at block 42. In the present example, when BO2 is finished being processed, it is removed from the dynamic list, as follows:

| Parameter Input Agent for BO77 | → behavior objects in dynamic list |
|---|---|
| pe24 | → dynamic list of parameters |

The list is then examined to determine whether there are any behavior objects, as shown at block 44. If there are any behavior objects, the flow diagram loops back to block 36 for an additional iteration to process the behavior objects in the dynamic list. If there are no behavior objects in the list, the flow diagram loops back to block 30 to check if an event has occurred.

In the present example, the dynamic list includes one behavior object (BO77). Assuming that, when repeating block 36, the processing of BO77 does not result in any change. Thus, when repeating block 38, no parameters output from the processed behavior object are changed, and no behavior objects are added to the dynamic list (block 40). When behavior object 77 is removed from the dynamic list (block 42), the dynamic list does not have any behavior objects and the transaction has completed (as far as the behavior engine is concerned).

Instead of assuming that the processing of BO77 does not result in any change, assume that BO77 does change pe8. After iterating through steps 36 through 42, the dynamic list is as follows:

| Parameter Input Agent for BO2 | → behavior objects in dynamic list |
|---|---|
| pe8 | → dynamic list of parameters |

Because the dynamic list has a behavior object, blocks 36 through 44 are again repeated. After updating BO2, and assuming parameters pe17 and pe56 change, the dynamic list is as follows:

| Parameter Input Agent for BO31 | Parameter Input Agent For B077 | → behavior objects in dynamic list |
|---|---|---|
| pe17 | pe56 | → dynamic list of parameters |

After updating B031, and assuming parameter pe5 was changed, the dynamic list is as follows:

| Parameter Input Agent for BO77 | → behavior objects in dynamic list |
|---|---|
| pe5 | → dynamic list of parameters |
| pe56 | |

Finally, B077 will be updated. In this iteration, it is unlikely that updating BO77 will change pe8 since the previous updating of BO77 has changed pe8 in this transaction. However, the updating of BO77 may change pe8 since in a previous iteration, the updating of BO77 did so with other variables. In the event that pe8 changes, BO2 will be updated because of this change.

After a finite number of iterations, the dynamic list shrinks to zero. The iterations allow for the 'revisiting' of an already updated behavior object to allow these circular dependencies to exist. Further, only the behavior objects which have potentially changed are processed or updated. As discussed above, rather than requiring that all behavior objects (including all of the algorithms within a behavior object) are processed, one aspect of the present invention allows for updating only of the behavior objects which have input parameters which have changed. Further, for the processed behavior objects, only the algorithms which include a changed parameter need to be processed. This allows for much more efficient and rapid processing of events.

Moreover, with the iterations, it is not guaranteed that all input parameters to a given behavior object are in a consistent or steady state for the given transaction until the transaction has completed. For example, if relational lookup tables are used by the behavior objects, and the input parameters are foreign keys to those lookup tables (e.g., if algorithms in a behavior object reference parameters other than those input), an invalid lookup may be performed. To solve this problem, "latent" parameters may be used. This allows a behavior object to put itself into a "latent" state with regard to a parameter's, or set of parameters', dependency until all other dependencies have been processed. The input parameters would then be at a steady state and could be used for the table lookup. An additional list, one of behavior objects to be called during the update for latent parameters, and their latent parameters, is maintained by the Behavior Engine. The behavior objects add themselves and their latent parameters to the list during the normal transaction processing. For example, if a behavior object is dependent on a "latent" parameter, both the behavior object and the latent parameters may be added to the latent parameter list. After all non-latent parameter dependencies have been handled during the transaction, the behavior objects with latent parameters are updated one additional time for the dependencies.

Discussed above is an example of a user input which causes a transaction. Where a system input, such as due to a setup or configuration, causes a transaction, different types of parameters may be initially changed. For example, parameters which are parameter output agents (outputs to behavior objects) may change and initiate a transaction as well. In FIG. 1, an example of a parameter which may change due to system input is pe56. In this instance, if pe56 has changed, it may also effect another output to BO2. Therefore, prior to building the dynamic list, BO2 is updated using the changed pe56 to determine if the change affects pe17. After updating, the dynamic list is created and the processing proceeds as described above. For example, if the change to pe56, and updating of BO2 changes pe17, BO31 and BO77 are placed on the dynamic list.

It should be noted that each of the acts in the method shown in FIG. 3 can be performed by executing computer-readable program code stored on computer-usable media (e.g., one or more memories or disk drives). For example, the computer-readable program code implementing the functionality of automatically selecting a set of medical images based on acquisition time control settings can be stored in computer-usable media in the ultrasound system 10.

As noted above, although ultrasound images were used to illustrate the preferred embodiments, any type of medical image can be used. Medical images include still or moving images ("clips") generated from any imaging modality including, but not limited to, ultrasound, computed tomography (CT), magnetic resonance imaging (MRI), computed radiography, magnetic resonance, angioscopy, color flow Doppler, cystoscopy, diaphanography, echocardiography, fluoresosin angiography, laparoscopy, magnetic resonance angiography, positron emission tomography, single-photon emission computed tomography, x-ray angiography, computed tomography, nuclear medicine, biomagnetic imaging, culposcopy, duplex Doppler, digital microscopy, endoscopy, fundoscopy, laser surface scan, magnetic resonance spectroscopy, radiographic imaging, thermography, and radio fluroscopy. The following claims should not be limited to a specific type of medial image unless explicitly recited therein.

It is intended that the foregoing detailed description be understood as an illustration of selected forms that the invention can take and not as a definition of the invention. It is only the following claims, including all equivalents, that are intended to define the scope of this invention.

What is claimed is:

1. In a medical imaging system having a behavior engine with behavior objects interconnected by parameters, at least one parameter being circularly dependent on another parameter, a method for handling a changed parameter for a given transaction comprising:
   changing at least one parameter;
   accessing a static list, the static list comprising the parameters and associated behavior objects;
   generating a dynamic list, based on the static list, of behavior objects dependent on the changed parameter;
   iteratively:
      processing the behavior objects in the dynamic list;
      determining whether any output parameters from the processed behavior objects have changed;
      adding behavior objects to the dynamic list which are dependent on the changed parameter outputs; and
      removing the processed behavior objects from the dynamic list.

2. The method of claim 1, further comprising, upon initialization of the behavior engine, building the static list of the parameters and the behavior objects associated with the parameters.

3. The method of claim 1, wherein the behavior objects associated with the parameters comprises the behavior objects which have, as input, the parameters, and the behavior objects which have, as output, the parameters.

4. The method of claim 1, wherein changing a value of at least one parameter comprises modifying the value of the parameter as a result of a user input.

5. The method of claim 1, wherein the method iterates until the dynamic list has no behavior objects.

6. The method of claim 1, wherein for the given transaction, the behavior object dependent on the changed parameter is processed more than once.

7. The method of claim 1, further comprising updating the medical imaging system based on the parameters.

8. In a medical imaging system having a behavior engine with behavior objects interconnected by parameters, a method for handling a changed parameter for a given transaction comprising:
   changing at least one parameter due to user input,
   accessing a static list, the static list comprising the parameters and associated behavior objects; and
   determining whether parameters, other than the changed parameter, are changed for the given transaction, the step of determining consisting of processing, based on the static list and the changed parameter, fewer than all of the behavior objects in the behavior engine.

9. The method of claim 8, wherein determining whether parameters are changed for the given transaction consists of processing behavior objects which have a changed input parameter.

10. The method of claim 9, wherein processing behavior objects which have a changed input parameter comprises processing a particular behavior object more than once.

11. The method of claim 9, wherein at least some of the behavior objects comprise algorithms dependent on input parameters, and
   wherein processing behavior objects consists of processing algorithms which are dependent on the changed input parameter.

12. The method of claim 8, wherein at least one parameter in the behavior engine is circularly dependent on another parameter.

13. The method of claim 8, wherein processing fewer than all of the behavior objects in the behavior engine is performed dynamically.

14. The method of claim 8, wherein processing fewer than all of the behavior objects in the behavior engine comprises a processing sequence determined by the changed parameter.

15. The method of claim 8, wherein processing fewer than all of the behavior objects in the behavior engine comprises first processing the behavior objects which have, as input, the changed parameter.

16. Medical imaging apparatus comprising:
   processor;
   storage device in communication with the processor;
   display in communication with the processor;
   user interface in communication with the processor, wherein the storage device comprises:
- code for behavior engine comprising behavior objects interconnected by parameters;
- static list comprising the parameters and associated behavior objects;
- code for changing at least one parameter due to user input from the user interface;
- code for determining whether parameters, other than the changed parameter, are changed for a transaction consisting of processing, based on the static list and the changed parameter, fewer than all of the behavior objects in the behavior engine; and
- code for rendering an image on the display based on the changed parameters.

17. The medical imaging apparatus of claim 16, further comprising in the storage device:
- code for generating the static list based on the behavior engine.

18. The medical imaging apparatus of claim 16, wherein the code for changing at least one parameter due to user input from the user interface comprises an event handler.

19. The medical imaging apparatus of claim 16, wherein the code for processing, based on the static list and the changed parameter, fewer than all of the behavior objects in the behavior engine is configured to perform the following steps:
- generating a dynamic list, based on the static list, of behavior objects dependent on the changed parameter;
- iteratively:
    - processing the behavior objects in the dynamic list;
    - determining whether any output parameters from the processed behavior objects have changed;
    - adding behavior objects to the dynamic list which are dependent on the changed parameter outputs; and
    - removing the processed behavior objects from the dynamic list.

20. The medical imaging apparatus of claim 19, wherein the code iterates until the dynamic list has no behavior objects.

21. The medical imaging apparatus of claim 16, further comprising:
- a beamformer in communication with the processor; and
- a transducer in communication with the beamformer.

* * * * *